United States Patent [19]

Scholz et al.

[11] Patent Number: 4,985,280

[45] Date of Patent: Jan. 15, 1991

[54] PROCESS FOR HYDROPHOBIZATION OF MICROBACTERIA RETAINING AIR FILTER

[75] Inventors: Ralph-Peter Scholz, Lichtenberg; Volker Glöckner, Oberbobritzsch, both of German Democratic Rep.

[73] Assignee: VEB Kombinat Medizinund Labortechnik Leipzig, Leipzig, German Democratic Rep.

[21] Appl. No.: 356,644

[22] Filed: May 22, 1989

Related U.S. Application Data

[63] Continuation-in-part of Ser. No. 103,981, Oct. 1, 1987, abandoned.

[30] Foreign Application Priority Data

Dec. 22, 1986 [DD] German Democratic Rep. .... 298191

[51] Int. Cl.[5] .................... B05D 5/00

[52] U.S. Cl. .................... 427/244; 427/247; 427/384

[58] Field of Search .................... 427/244, 384, 247

[56] References Cited

U.S. PATENT DOCUMENTS

| | | | |
|---|---|---|---|
| 3,010,536 | 11/1961 | Plurien et al. | 427/244 |
| 3,053,762 | 9/1962 | Adiletta | 210/507 |
| 3,625,734 | 12/1971 | Ward | 427/244 |
| 4,169,754 | 10/1979 | Perotta | 427/244 |
| 4,210,697 | 7/1980 | Adiletta | 427/244 |
| 4,232,087 | 11/1980 | Trask | 427/244 |
| 4,376,140 | 3/1983 | Kimoto et al. | 427/244 |
| 4,413,074 | 11/1983 | Wrasidlo et al. | 427/244 |
| 4,557,955 | 12/1985 | Walch et al. | 427/244 |
| 4,720,334 | 1/1988 | DuBois et al. | 427/244 |

*Primary Examiner*—Janyce Bell

*Attorney, Agent, or Firm*—Jordan and Hamburg

[57] ABSTRACT

The invention concerns a process for hydrophobation of materials for microbacteria-retaining air filters which are preferentially used for blood transfusion and therapy by infusions. Fluorocarbons or their compounds are used for surface coating of filter materials, the contacting of which are effected either by spraying or by immersion. During these procedures, the hydrophobating agent can be in the form of either a solution, emulsion, or in pure form.

5 Claims, No Drawings

PROCESS FOR HYDROPHOBIZATION OF MICROBACTERIA RETAINING AIR FILTER

This application is a continuation-in-part, of application Ser. No. 103,981, filed Oct. 1, 1987, now abandoned.

BACKGROUND OF THE INVENTION

The invention concerns a process for hydrophobization of microbacteria-proof air filter materials. Using this process such air filter materials are made hydrophobic for the purpose of retaining microparticles and microbial components of air and which are preferentially used in blood transfusion services, for infusion therapy, and in anaesthesia and surgery.

In almost all the fields of medicine, procedures are known during which liquids contained in a receptacle have to be conveyed to patients or to other containers. Often the transfer is possible only with simultaneous venting of the receptacles during use. In most cases, the moved volume is atmospheric air, which before reaching the respective receptacles has to be cleaned of microparticles. Cleaning of the air is effected by means of filter materials such as ceramics, papers, fleeces and membranes (compare Wirtschaftspatent WPB ol D/293 811.1, DD), which during this process or during interruptions for medical reasons may come into contact, with the liquids to be infused. This contact however, should always be avoided, since otherwise clogging of the filter pores may arise also a nutritive substrate for the conveyed microorganisms may originate. If this occurs, contamination of the transfer line may no longer be excluded, causing the transfer set as well as the preserved liquid to have to be discarded.

Therefore, the agents of hydrophobation used must meet special requirements. This means that they have to be physiologically unobjectionable, since they may come into contact both with air as well as with the liquids to be infused. Furthermore, the use of the hydrophobizing agent should not cause clogging of the filter pores and the hydrophobic effect must be maintained over a period of about 5 years.

The current level of technology is characterized by two procedures. In the first case, filter materials are used, which due to their chemical structure are already hydrophobic, e.g., membranes from polyethyleneterephthalate. In the second case, filter materials are used, which subsequently have to be treated with hydrophobizing agents.

The first-mentioned filter materials are suitable for use, with venting under a small differential pressure, but are relatively expensive to manufacture. The filters made of ceramics, paper, glass fleece, textiles, leather, or of other materials, which are hydrophobized subsequently, are considerably more simple to manufacture. Before put into use, however, they have to be treated unilaterally with a hydrophobizing agent which meets the respective requirements. The most well-known agents among them are paraffins, waxes, metallic soaps, with additives of aluminium- and zirconium salts, quarternary organic compounds, derivatives of urea, fatty acid modified melamine resins, complex chromium salts and silicone. During hydrophobization, the filter material maintain their porosity because of impregnation in the coating of individual fibres (see Römpps Chemie Lexikon, $8^{th}$ Edition Frankh'sche Verlagshandlung, Stuttgart 1983). One hint given in the same source, stating that perfluoridized compounds also are suitable for hydrophobization, although they are predominantly used in oleophobation and soil resistance equipment, is of no importance for a process of hydrophobization of microbacteria-proof materials for air filters.

SUMMARY OF THE INVENTION

It is the aim of this invention to exclude the drawbacks of known technical solutions and to manufacture a filter material which completely meets hygienic requirements.

In the first place, hydrophobization has to exclude any impairment of permeability of the filter by the media to be filtered. Furthermore, processes of sterilization should not exert any influence on the efficacy of the hydrophobizing agent. In addition a maximum shelf life of 5 years, which has not been attained until now, must be achieved.

Present invention is directed to developing a process for hydrophobization of porous materials made from ceramics, textile fleece, glass fleece, etc., or of nuclear track filter foil, as well as a hydrophobizing agent for filters in vented systems. Furthermore, the hydrophobizing agent should be suitable for easy manufacture from local raw materials and should meet the requirements for hydrophobizing agents for air filters for medical purposes already in smallest concentrations.

According to the invention, this task is solved by a process of the initially defined kind wherein flurocarbons and their compounds serve as hydrophobizing agents for surface coating of filter materials, in which the hydrogen bonded to a carbon atom is completely substituted by fluorine, i.e., the hydrophobizing agents are perfluorocarbons. With this process, the surfaces to be treated have to be coated in a regular manner by a layer of such fluoridized links of $CF_3\,(CF_2)_n$ until the filter material shows an essentially fluoridized surface and obtains at the same time a critical internal surface tension, which is less than the the internal surface tension of the aqueous and liquid products, respectively.

DETAILED DESCRIPTION OF THE PREFERRED EMBODIMENTS

As hydrophobizing agents, there may be used emulsions of fluorine containing polymers or oligomers, in particular PTFE, functional groups carrying organic fluorine compounds, in particular perfluoroalkyl compounds, reactive organic fluorine compounds, in particular perfluoroalkenes, or mixtures of these compounds. A carrier substance R according to the invention, e.g., alkyl groups with a fluorine containing surface and high rejection of liquid will be obtained by groups having the formula 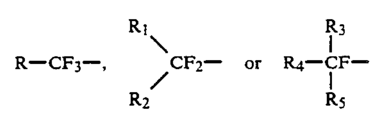 and their compounds, respectively.

The set up of groups and compounds, respectively, with the filter material may be achieved by known forms of chemical bonding or by physical interactions, e.g., by Van-der-Waals-forces.

With this process, the contact of the hydrophobizing agent with the filter material should be brought about preferentially by means of known procedures of spraying or immersing, wherein the fixation of the hydrophobizing agent is then effected by evaporation of the solvent.

The process of the invention and compositions employed therein involve no active ingredient other than the hydrophobizing agent or agents, i.e., no ingredient other than the hydrophobizing agent or agents and mere carrier therefor.

By means of wherein fluorcarbons for surface coating of several filter materials an air filter material is obtained, which under the given conditions is not wettable. With the execution of the procedure according to the invention, a fluorine containing filter surface is obtained, which by far surpasses the effect of the conventional hydrophobizing agents.

While paraffins and polyolefins respectively, e.g., PE, show critical surface tensions of 31 nN/m, surface tensions using —$CF_2$ -surfaces of only 18 nN/m and using pure —$CF_2$-surfaces of only 6 mN/m are attained (see L. Lichtenberger, chim. et Ind., Paris 104 (1971) 7, page 815). Thus, a higher degree of safety is provided, because a lower critical interfacial tension impedes the wettability of solids. This aspect is of particular importance with blood substitutes, since these liquids in part show considerably lower surface tensions in comparison to water (72 nN/m).

It has been found that liquid repulsion depends on the principle that the lower the interfacial tension, the less solids are wettable.

Therefore, the process according to the invention consists in rendering air filter materials hydrophobic by the application of fluorinated carbons and their compounds. Herewith, the surfaces to be treated must be coated with a layer of fluoridized links of $CF_3 (CF_2)_n$. In this context hydrophobation is preferentially effected by means of the procedures of spraying and immersing, which bring the hydrophobating agent into contact with the filter material in the best manner. The hydrophobizing agent may be applied either in solution, emulsion, or in pure form.

Fixation on the filter material according to its kind is effected by simple drying, consequently by evaporation of the solvent, by thermal treatment, or by means of other forms of activation, e.g., radiation with electrons, or in a given case by a combination of these forms of treatment. A process of cleansing using solvents and/or other suitable washing agents, e.g., twofold distilled water (*Aque redestillata* or *bidestillata*) in order to remove excessive fluorinated carbons and adjuvants follows.

With the application of fluorinated carbons and their compounds, respectively, as a surface coating according to the invention, an air filter material consisting of ceramics, textile fleece, glass fleece and the like, or nuclear track microfilter foil, may be used.

Furthermore, in the case of using fluorinated carbons and their compounds for hydrophobization, emulsions of fluorine containing polymers or oligomers, in particular PTFE, functional groups carrying organic fluorinated compounds, in particular perfluoroalkyl compounds, reactive organic fluorine compounds, inert fluorine alkyl compounds, e.g. perfluoroalkanes, or mixtures of these compounds may also be used.

If e.g., the filter material is glass fleece and a perfluoroalkane/alkene (i.e., perfluoralkane/perfluoroalkene) mixture of a chain length of about $C_5$–$C_8$ is used as the hydrophobizing agent, this is simply sprayed on the surface of the material with due consideration of respective safety regulations (e.g., using an exhaust hood) causing a mass increase between 0.1 and 1.0%. Subsequent to a drying process between 50° and 100° C. in a drying chamber, the glass fleece is successively washed using acetone and ethanol followed by washing it twice with bidistilled water. After drying at 80° C. for 3 hours, the hydrophobized filter material is ready for use.

The relationship to different filter materials such as ceramic substances, paper, glass- or textile fleece is defined in a manner that an unwettable venting filter, which is hydrophobized according to the invention and is microbacteria proof, gyaranters a minimum throughput of 100 ml air min$^{-1}$. It thus fulfills hygienic requirements because the transmission ratio of the filter for the media to be filtered is not impeded by the process of hydrophobization.

With the provision of a fluorine containing surface of the following groups, or of their compounds, such as

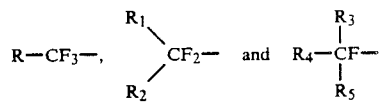

by means of which, as has already been described, a filter material may be manufactured on the basis of physical interactions and forms of chemical bonding, respectively, an until now unknown level of efficacy with respect to liquid rejection is achieved.

We claim:

1. A process for hydrophobing air filter materials for retaining microbacteria, comprising applying to an air filter material selected from the group consisting of ceramics, textile fleece, glass fleece and nuclear track microfilter foil a hydrophobing composition consisting of at least one perfluorocarbon or a solution or suspension thereof, the composition containing no other active ingredient, said perfluorocarbon being a mixture of a perfluoroalkane and a perfluoroalkene.

2. A process according to claim 1, wherein the critical internal surface tension of the applied perfluorocarbon is 18 nN/m or less.

3. A process according to claim 2, wherein the coated air filter material has a minimum throughput of 100 ml of air per minute.

4. A process according to claim 1, in which the carbon chain lengths of the perfluoroalkane and the perfluoroalkene are 5 to 8.

5. A process according to claim 4, in which the air filter materials consist of ceramics.

* * * * *